United States Patent
Li et al.

(10) Patent No.: US 10,101,810 B2
(45) Date of Patent: Oct. 16, 2018

(54) DEVICE FEEDBACK AND INPUT VIA HEATING AND COOLING

(75) Inventors: Kevin Ansia Li, Chatham, NJ (US); Brian Amento, Morris Plains, NJ (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 1183 days.

(21) Appl. No.: 13/305,224

(22) Filed: Nov. 28, 2011

(65) Prior Publication Data

US 2013/0135214 A1    May 30, 2013

(51) Int. Cl.
| | | |
|---|---|---|
| G06F 3/0488 | (2013.01) | |
| G06F 3/01 | (2006.01) | |
| G09F 19/00 | (2006.01) | |
| A61B 5/00 | (2006.01) | |

(52) U.S. Cl.
CPC .............. G06F 3/016 (2013.01); G09F 19/00 (2013.01); *A61B 5/681* (2013.01); *G09G 2320/041* (2013.01)

(58) Field of Classification Search
CPC ....... G06F 3/041; G06F 3/0412; A61B 5/681; A61B 5/7267
USPC .................................................. 345/173–174
See application file for complete search history.

(56) References Cited

U.S. PATENT DOCUMENTS

| | | | | |
|---|---|---|---|---|
| 6,362,740 B1* | 3/2002 | Jung | | 340/584 |
| 2005/0183143 A1* | 8/2005 | Anderholm | | G06F 11/32 |
| | | | | 726/22 |
| 2006/0206833 A1* | 9/2006 | Capper | | H04M 1/7253 |
| | | | | 715/773 |
| 2008/0158172 A1* | 7/2008 | Hotelling | | G06F 1/3231 |
| | | | | 345/173 |
| 2009/0195512 A1* | 8/2009 | Pettersson | | G06F 3/016 |
| | | | | 345/173 |
| 2012/0068952 A1* | 3/2012 | Slaby | | G01K 7/02 |
| | | | | 345/173 |

FOREIGN PATENT DOCUMENTS

WO    WO 2009007952 A3 *  3/2010

OTHER PUBLICATIONS

Wilson, Graham, Thermal Feedback for Mobile Devices, May 7, 2011; pp. 1-8.*
Wilson, G. et al., "Some Like it Hot? Thermal Feedback for Mobile Devices," CHI 2011, May 7-12, 2011.

* cited by examiner

*Primary Examiner* — Kent Chang
*Assistant Examiner* — Sujit Shah
(74) *Attorney, Agent, or Firm* — Hartman & Citrin LLC (57) ABSTRACT

A thermoelectric display including an array of thermoelectric devices is used to provide output to a user in the form of thermal feedback. The thermal feedback may be used to provide navigation cues to the user to enable eyes-free navigation. The thermal feedback may be used to provide target acquisition cues to enable the user to accurately target a contact point on a touchscreen. The thermal feedback may be used to convey an emotive aspect of a message to the user. The thermal feedback may be used to identify to the user a caller associated with an incoming call. The thermoelectric display may be, alternatively or additionally, used to provide input to another device, such as a mobile device to which the thermoelectric display is operatively coupled.

18 Claims, 10 Drawing Sheets

DEVICE FEEDBACK AND INPUT VIA HEATING AND COOLING

BACKGROUND

A sensory system is responsible for processing sensory information. A sensory system typically consists of sensory receptors, neural pathways, and regions of the brain involved in sensory perception. The five commonly recognized sensory systems are the vision system, the auditory ("hearing") system, the somatic ("touch") system, the taste system, and the olfaction ("smell") system.

User interfaces allow an individual to control or otherwise interact with computers, smartphones, tablets, and other electronic devices. User interfaces leverage human sensory systems to convey information to an individual. User interfaces convey information to individuals in a variety of types, the most common of which include audio feedback, visual feedback, and vibrotactile feedback. Many user interfaces combine multiple forms of feedback.

While audio, visual, and vibrotactile feedback are useful in many situations, each of these feedback types may be too conspicuous for certain situations. Audio feedback is the most conspicuous and is likely to be the first feedback type to be turned off if the user does not want others within his or her vicinity to be aware of an event, such as an incoming call or message, occurring on their device. Visual feedback, although more discrete than audio feedback, may be viewed by others on purpose or inadvertently. Vibrotactile feedback, although also more discrete than audio feedback, may be itself contributory to the production of sound. Thus, none of today's available feedback types can be considered truly inconspicuous.

SUMMARY

Concepts and technologies are described herein for device feedback and input via heating and cooling. In accordance with some of the concepts and technologies disclosed herein, a thermoelectric display including an array of thermoelectric devices is used to provide output to a user in the form of thermal feedback. The thermal feedback may be used to provide navigation cues to the user to enable eyes-free navigation. The thermal feedback may be used to provide target acquisition cues to enable the user to accurately target a contact point on a touchscreen. The thermal feedback may be used to convey an emotive aspect of a message to the user. The thermal feedback may be used to identify to the user a caller associated with an incoming call. The thermoelectric display may be, alternatively or additionally, used to provide input to another device, such as a mobile device to which the thermoelectric display is operatively coupled.

According to one aspect disclosed herein, a thermoelectric display includes an array of thermoelectric devices, each of which is configured to undergo a temperature change in response to an electric current being induced therein, and to utilize the temperature change as an input to a device.

According to another aspect disclosed herein, a method for conveying information to a user via thermal feedback includes, in response to an event, receiving, at a thermoelectric display including an array of thermoelectric devices, instructions to change a temperature of a thermoelectric device of the array of thermoelectric devices to convey information associated with the event to a user, and, in response to receiving the instructions, changing the temperature of the thermoelectric device of the array of thermoelectric devices thereby providing thermal feedback to the user, the thermal feedback being indicative of the information associated with the event.

According to yet another aspect disclosed herein, a mobile device includes a thermoelectric display, which includes an array of thermoelectric devices, each of which is configured to undergo a temperature change in response to an electric current being applied thereto. The mobile device further includes a processor in communication with the thermoelectric display, and a memory in communication with the processor. The memory includes instructions which, when executed by the processor, cause an electric current to be applied to a thermoelectric device of the array of thermoelectric devices, thereby causing the thermoelectric device to undergo a temperature change and, as a result, provide thermal feedback to a user.

It should be appreciated that the above-described subject matter may be implemented as a computer-controlled apparatus, a computer process, a computing system, or as an article of manufacture such as a computer-readable storage medium. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DETAILED DESCRIPTION

While the subject matter described herein may be presented, at times, in the general context of program modules that execute in conjunction with the execution of an operating system and application programs on a computer system, those skilled in the art will recognize that other implementations may be performed in combination with other types of program modules. Generally, program modules include routines, programs, components, data structures, and other types of structures that perform particular tasks or implement particular abstract data types. Moreover, those skilled in the art will appreciate that the subject matter described herein may be practiced with other computer system configurations, including hand-held devices, mobile devices, wireless devices, multiprocessor systems, microprocessor-based or programmable consumer electronics, minicomputers, mainframe computers, routers, switches, and the like.

In the following detailed description, references are made to the accompanying drawings that form a part hereof, and in which are shown by way of illustration specific embodiments or examples. Referring now to the drawings, in which like numerals represent like elements throughout the several figures, aspects of a computing system, computer-readable storage medium, and computer-implemented methodology for providing device feedback and input via heating and cooling will be presented.

Figure 1:
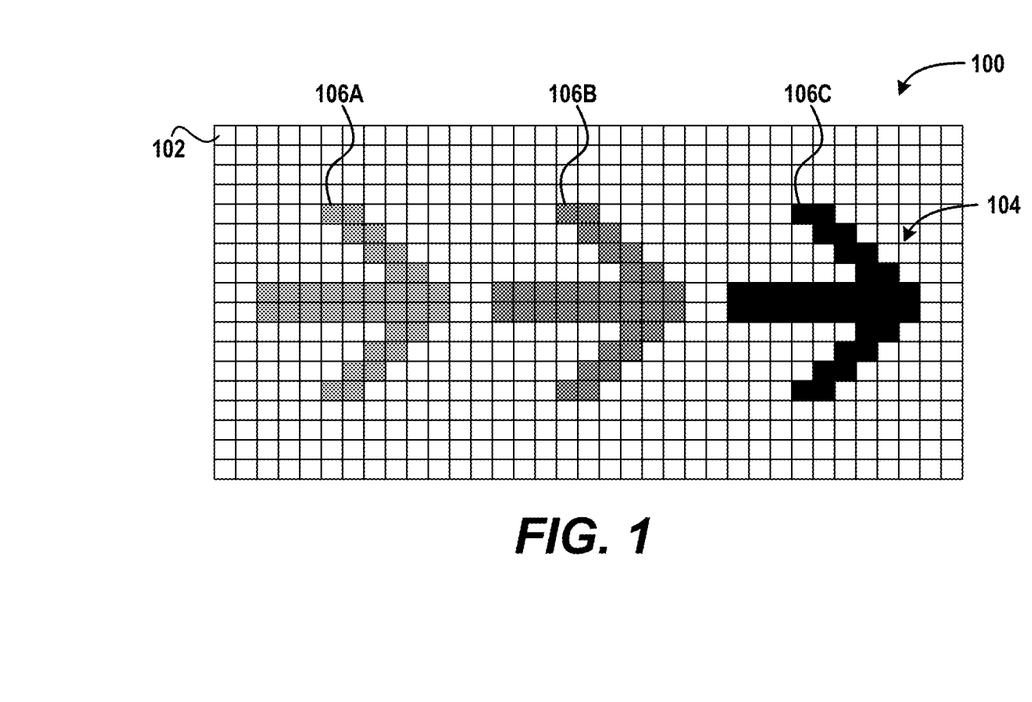
FIG. 1 is a diagram illustrating aspect of a thermoelectric display, according to an illustrative embodiment.

Referring now to FIG. 1, aspects of a thermoelectric display 100 will be described, according to an illustrative embodiment. In some embodiments, the thermoelectric display 100 is configured to operate as an output mechanism for conveying information to a user via thermal feedback, as will be described in greater detail herein. In some embodiments, the thermoelectric display 100 is configured to operate as an input mechanism for receiving input from a user. In some embodiments, the thermoelectric display 100 is used to determine a location of a device to which the thermoelectric display 100 is operatively coupled, as also will be described in greater detail herein.

It should be understood that although the term display is used herein to describe the thermoelectric display 100, the term display in this context refers to the ability of the thermoelectric display 100 to present information to a user utilizing thermal feedback. Moreover, although the thermoelectric display 100 may reveal an image provided by radiation in the infrared range of the electromagnetic spectrum emitted by the thermoelectric display 100 when viewed utilizing a thermal imaging device such as a thermal camera, the thermoelectric display 100 is primarily configured to convey information to a user through a user touching the thermoelectric display 100. Other references herein to the term display may refer to a device configured to convey information to a user in a visual manner.

The illustrated thermoelectric display 100 includes an array of thermoelectric devices 102. In some embodiments, the thermoelectric devices 102 are solid-state devices. In some embodiments, the thermoelectric devices 102 are Peltier devices, which are solid-state active heat pumps configured to transfer heat from one side of the device to the other side against the temperature gradient (i.e., from cold to hot) with the consumption of electrical energy. In these embodiments, when direct current flows through one or more of the thermoelectric devices 102, heat is moved from one side of the one or more of the thermoelectric devices 102 to the other thereby causing the thermoelectric display 100 or a portion thereof to be heated or cooled. In some embodiments, the heated and/or cooled portions of the thermoelectric display 100 are used separately or together to convey information to a user when the user touches the thermoelectric display 100. In some embodiments, the heated and/or cooled portions of the thermoelectric display 100 are heated and/or cooled at one or more frequencies such that the user experiences various heating and/or cooling sensations, which may be used to convey different types of information to the user.

Heating and/or cooling of one or more portions of the thermoelectric display 100 is represented in the illustrated embodiment as a thermal image 104. The thermal image 104 is used to convey information to a user through thermal feedback when the user touches the thermoelectric display 100. In the illustrated embodiment, a voltage has been applied to some of the thermoelectric devices 102 resulting in the thermal image 104 being presented on the thermoelectric display 100. When a user touches the thermoelectric display 100, the user will sense the thermal image 104 through their somatic sensory system. It is contemplated that the user may need to be trained to associate a particular thermal image with information that is meant to be conveyed. Some thermal images, such as the indication of a direction as will be described in greater detail herein below, may be readily apparent without the need for additional training.

The illustrated thermal image 104 consists of three portions 106A, 106B, 106C, each of which resembles an arrow and includes a portion of the thermoelectric devices 102 that have been heated to a different temperature. This variation in temperature is illustrated from light gray, to gray, and then to black, with the light gray indicating the lowest temperature and the black indicating the highest temperature. The illustrated thermal image 104 may be indicative of a direction to be conveyed to a user through the arrow shape of the thermal image 104 and the increasing temperature in the direction of the arrow head.

It should be understood that a thermal image may employ one or more of the thermoelectric devices 102, each of which may be set to operate at a static temperature or may vary in temperature to create the thermal image or a portion thereof. It also should be understood that a thermal image may be any shape and may be any size within the physical dimensions of the particular thermoelectric display upon which it is displayed.

In some embodiments, the thermoelectric display 100 is configured to be applied to a surface of another device or a component thereof such as, but not limited to, a visual display device, a touchscreen device, a mobile device, a computer, a tablet device, a gaming system, or a peripheral device. In some embodiments, the thermoelectric display 100 is configured to be applied to a surface of an object such as, but not limited to, a steering wheel, a table, a desk, a chair, or an appliance.

Figure 2:
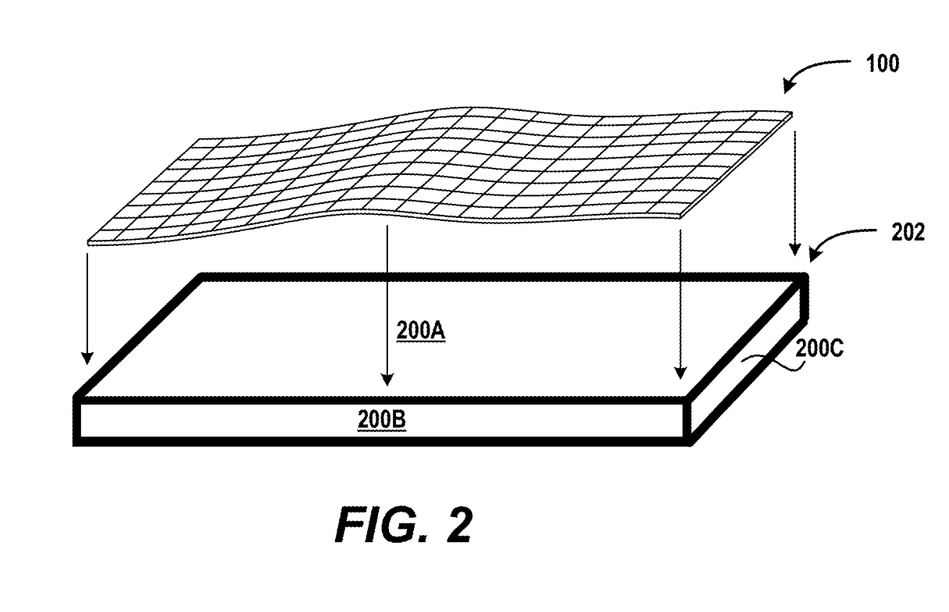
FIG. 2 is a diagram illustrating aspects of a thermoelectric display being applied to a surface of a device or object, according to an illustrative embodiment.

Turning briefly to FIG. 2, the thermoelectric display 100 is illustrated as being applied to a surface 200A of a device 202. In the illustrated embodiment, the thermoelectric display 100 is appropriately proportioned to cover the surface 200A, wherein the surface 200A is planar. In some embodiments, the thermoelectric display 100 is appropriately proportioned to cover multiple planar surfaces, such as the surfaces 200A, 200B, 200C and/or others (not shown). In some embodiments, the thermoelectric display 100 is appropriately proportioned to cover a non-planar surface.

The thermoelectric display 100, in some embodiments, is built-in to a case that is configured to enclose the device 202. In these embodiments, a connector may be provided within the case to operatively couple the thermoelectric display 100 to the device 202 for power and/or data transmission. In some embodiments, the thermoelectric display 100 is self-powered. In some embodiments, the case is configured to provide power to the thermoelectric display 100.

In some embodiments, the thermoelectric display 100 is built-in to the device 202. In these embodiments, the thermoelectric display 100 may be built-in to an external surface of the device 202, such as one or more of the surfaces 200A, 200B, 200C and/or others. Alternatively or additionally, in these embodiments, the thermoelectric display 100 may be built-in to a visual display portion of the device 202. The visual display portion, in some embodiments, includes a protective layer, a touchscreen layer, and a display layer. The thermoelectric display 100 may be positioned above, beneath, or between any of these layers.

Figure 3:
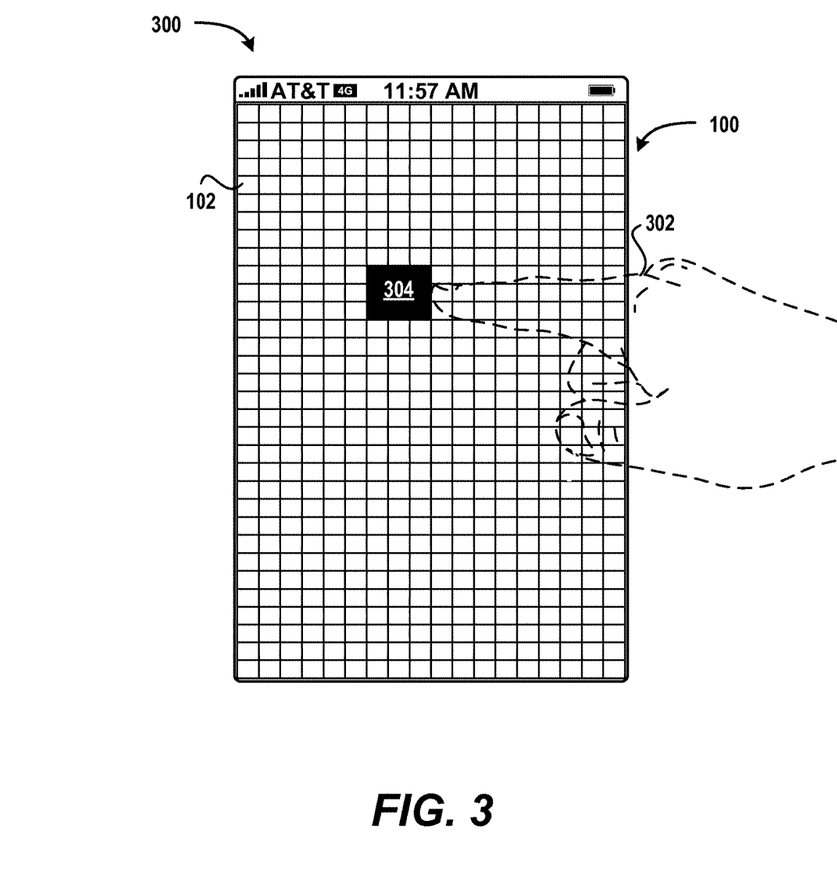
FIG. 3 is a user interface diagram illustrating aspects of a thermoelectric display for use as an input device, according to an illustrative embodiment.

Turning now to FIG. 3, a user interface 300 is shown as being displayed on a display of a device, such as a smartphone, a tablet, or other mobile computing device. The thermoelectric display 100 including the plurality of thermoelectric devices 102 is also shown. It should be understood that the thermoelectric display 100 is shown in FIG. 3 for purposes of illustration and explanation and, in practice, may be configured such that it is not viewable to a user. For example, the thermoelectric display 100 may be positioned beneath a protective layer, a display layer, and a touchscreen layer of a device.

In the illustrated embodiment, a user has positioned a finger 302 over a portion 304 of the thermoelectric display 100. Heat generated by the user's body and, particularly, the user's finger 302 induces a current in some of the thermoelectric devices 102 included in the touched portion 304. In some embodiments, this input is used to interact with the device in lieu of other input, such as input via a touchscreen, keypad, or button. In some embodiments, this input is used in addition to other inputs. In some embodiments, the thermoelectric display 100 is configured to detect any touch and, in response, send a signal to the device to wake up the device from a sleep, idle, or other state.

Figure 4:
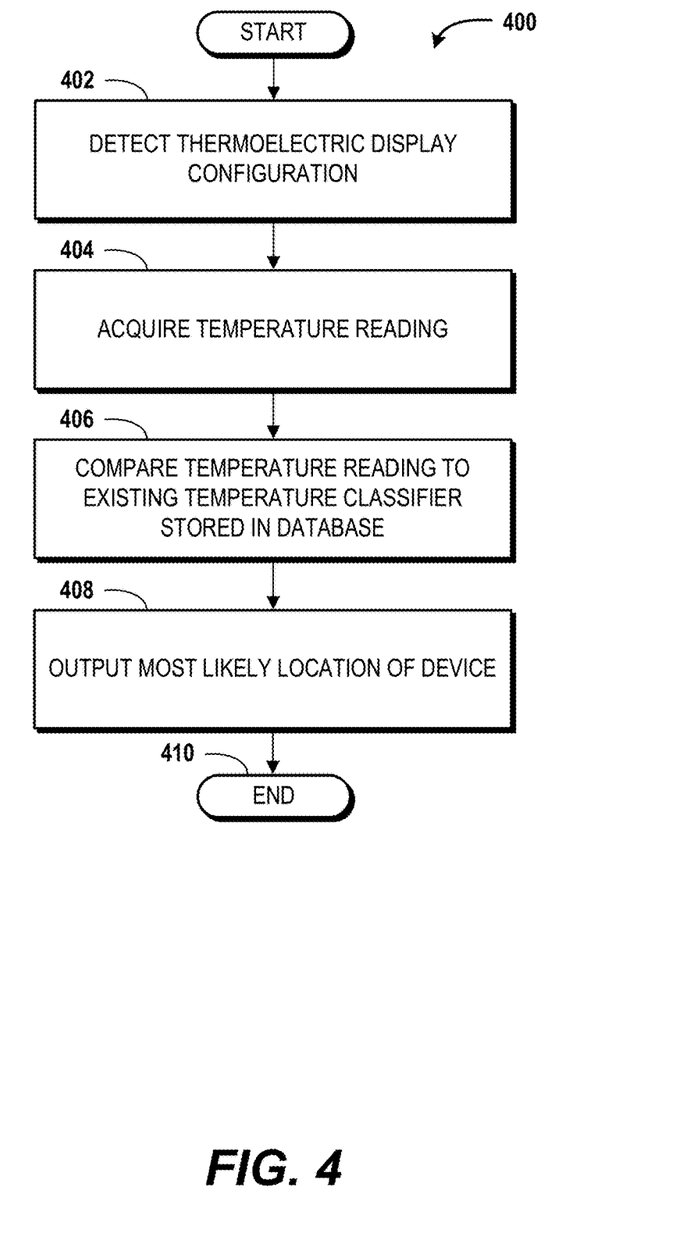
FIG. 4 is a flow diagram illustrating aspects of a method for using a thermoelectric display as an input device to determine a location of a device to which the thermoelectric display 100 is operatively coupled, according to an illustrative embodiment.

Turning now to FIG. 4, a flow diagram illustrating a method 400 for using the thermoelectric display 100 as an input device to determine a location of a device to which the thermoelectric display 100 is operatively coupled will be described, according to an illustrative embodiment. The method 400 is described in context of the thermoelectric display 100 being operatively coupled to another device. For ease of explanation and not limitation, the method 400 will be described in context of the thermoelectric display 100 being operatively coupled to a mobile device such as, but not limited to, a smartphone or other cellular telephone, a tablet, or other mobile computing device.

It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the appended claims.

It also should be understood that the illustrated methods can be ended at any time and need not be performed in its entirety. Some or all operations of the methods, and/or substantially equivalent operations, can be performed by execution of computer-readable instructions included on a computer-storage media, as defined below. The term "computer-readable instructions," and variants thereof, as used in the description and claims, is used expansively herein to include routines, applications, application modules, program modules, programs, components, data structures, algorithms, and the like. Computer-readable instructions can be implemented on various system configurations, including single-processor or multiprocessor systems, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These operations, structural devices, acts, and modules may be implemented in software, in firmware, in special purpose digital logic, and any combination thereof.

The method 400 begins and proceeds to operation 402, wherein the mobile device detects a configuration of the thermoelectric display 100. The configuration of the thermoelectric display 100 includes the location of one or more of the plurality of thermoelectric devices 102. In some embodiments, the configuration is reconfigurable such that one or more of the thermoelectric devices 102 are deactivated. In some embodiments, the configuration of the thermoelectric display 100 is reconfigurable via software stored within a computer-readable memory of the mobile device and executed by a processor of the mobile device. In some embodiments, the configuration of the thermoelectric display 100 is static or non-configurable. In some embodiments, operation 402 is configured to be performed once, such as during a setup process. This may be the case for embodiments in which the thermoelectric display 100 is non-configurable. Alternatively, in some embodiments, operation 402 is performed each time the method 400 is executed.

From operation 402, the method 400 proceeds to operation 404, wherein the mobile device acquires a temperature reading from the thermoelectric display 100. The temperature reading may be for one or more of the thermoelectric devices 102. From operation 404, the method 400 proceeds to operation 406, wherein the temperature reading is compared to an existing temperature classifier that is stored in a database. The database may be stored locally on the mobile device and/or may be stored in a network database with which the mobile device is configured to communicate.

In some embodiments, one or more temperature classifiers are determined and stored in the database during a setup procedure. In some embodiments, a user is prompted to position the mobile device in various locations on the user's body or within or attached to an article of clothing or an accessory. Illustrative locations include, but are not limited to, in hand, in between hands, in between a cheek and a shoulder, in between any two body parts of the user, in a pocket, in a pouch, or in any other location within an article of clothing or an accessory, such as a wallet, purse, bag, or a backpack. In these embodiments, heat generated by the environment in a given location and/or heat generated by the user's body induces a current within at least a portion of the thermoelectric devices 102 of the thermoelectric display 100. The resulting heat map is considered a classifier for a given location. For example, a classifier derived from placing the mobile device within a user's backpack will be different than a classifier derived from the user's holding the mobile device in hand. The classifier is associated with one or more locations within the database such that the comparison at operation 406 yields a likely location of the thermoelectric display 100 and, accordingly, also the mobile device.

In some embodiments, the determination of the most likely location of the mobile device is supplemented with output from one or more sensors included in the mobile device. These sensors may include, but are not limited to, an accelerometer, a global positioning system ("GPS") sensor, and a magnetometer sensor.

From operation 406, the method 400 proceeds to operation 408, wherein the mobile device outputs its most likely location. In some embodiments, the output in operation 408 is sent to an application executing on the mobile device. The application may be, but is not limited to, a telephone application, a messaging application, a social networking application, a game application, a productivity application, an email application, or another application executing on the mobile device that is, for one reason or another, configured to utilize a location of the mobile device to perform one or more functions.

An application may use the output to determine what kind of feedback to provide to a user. For example, if the output indicates that the location of the mobile device is the user's hand, the notification may be in the form of thermal feedback through the thermoelectric display 100. Alternatively, for example, if the output indicates that the location of the mobile device is in the user's backpack, where the user could not be notified via visual or thermal feedback, the notification may be in the form of audio feedback, such as a ringtone or other sound.

From operation 408, the method 400 proceeds to operation 410. The method 400 ends at operation 410.

Figure 5:
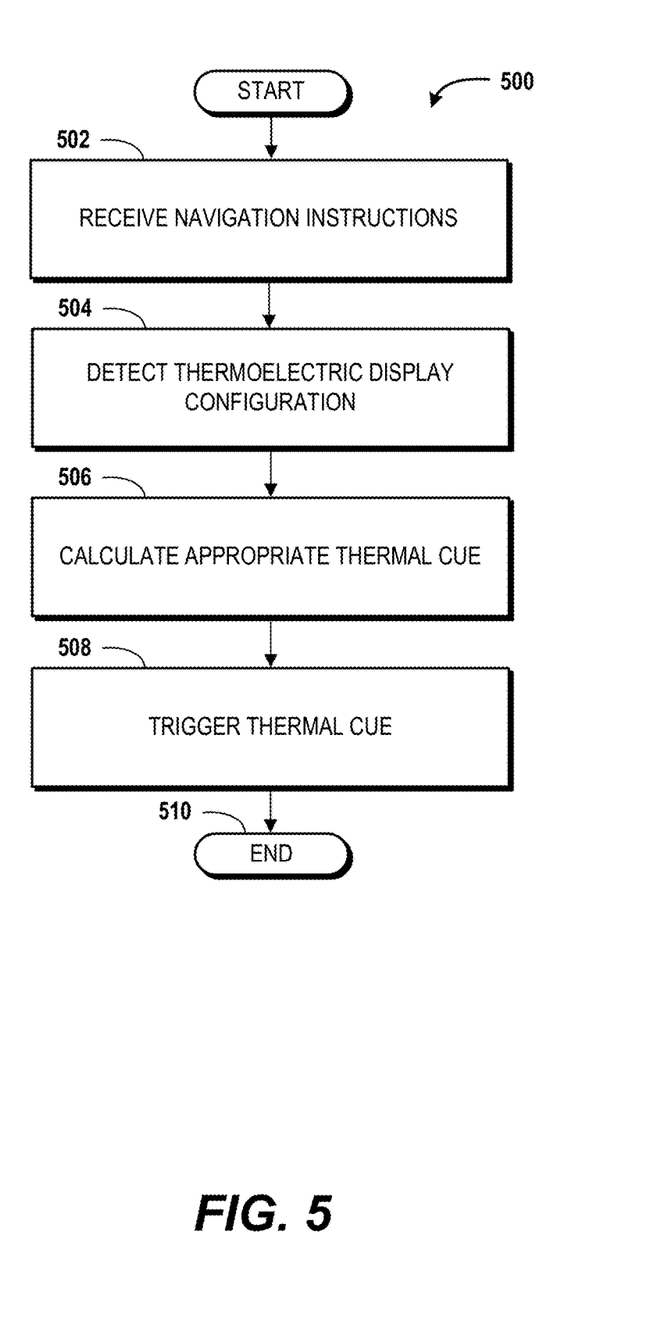
FIG. 5 is a flow diagram illustrating aspects of a method for using a thermoelectric display as an output device for a purpose of providing navigation instructions to a user, according to an illustrative embodiment.

Turning now to FIG. 5, a flow diagram illustrating a method 500 for using the thermoelectric display 100 as an output device for a purpose of providing navigation instructions to a user will be described, according to an illustrative embodiment. The method 500 is described in context of the thermoelectric display 100 being operatively coupled to another device. For ease of explanation and not limitation, the method 500 will be described in context of the thermoelectric display 100 being operatively coupled to a mobile device such as, but not limited to, a smartphone or other cellular telephone, a tablet, or other mobile computing device. The method 500 will also be described with reference to FIG. 6.

The method 500 begins at operation 502, wherein the mobile device receives navigation instructions. In some embodiments, the mobile device receives the navigation instructions from a network navigation database that is configured to send navigation instructions to the mobile device via a network such as, but not limited to, a mobile wireless data network or a WI-FI network. In some embodiments, the mobile device receives the navigation instructions from a local navigation database stored on the mobile device. The navigation instructions include a direction component and/or a location component. The direction component may include a compass direction and/or a relative direction. The location component may include a start position, an end position, and one or more intermediate positions, such as at direction changes, street changes, or other events during the navigation from the start position to the end position.

From operation 502, the method 500 proceeds to operation 504, wherein the mobile device detects a configuration of the thermoelectric display 100. The configuration of the thermoelectric display 100 includes the location of one or more of the plurality of thermoelectric devices 102. In some embodiments, the configuration is reconfigurable such that one or more of the thermoelectric devices 102 are deactivated. In some embodiments, the configuration of the thermoelectric display 100 is reconfigurable via software stored within a computer-readable memory of the mobile device and executed by a processor of the mobile device. In some embodiments, the configuration of the thermoelectric display 100 is static or non-configurable. In some embodiments, operation 402 is configured to be performed once such as during a setup process, such as a setup process for a navigation application executing on the mobile device. This may be the case for embodiments in which the thermoelectric display 100 is non-configurable. Alternatively, in some embodiments, operation 504 is performed each time the method 500 is executed.

From operation 504, the method 500 proceeds to operation 506, wherein the mobile device calculates an appropriate thermal cue. In some embodiments, the mobile device calculates an appropriate thermal cue based upon a preference setting established in a navigation application executing on the mobile device. In some embodiments, the mobile device calculates an appropriate thermal cue based upon the navigation instructions.

In some embodiments, the thermal cue includes a thermal image, such as the thermal image 104 described above with reference to FIG. 1. In some embodiments, the thermal cue includes a specific temperature, a variation of temperature over time, a variation of temperature according to one or more frequencies, one or more discrete points made up of one or more of the thermoelectric devices 102, and/or one or more thermal images 104 each made up of one or more of the thermoelectric devices 102. In some embodiments, the thermal cue includes triggering one or more of the thermoelectric devices 102 out of phase at different frequencies. In some embodiments, the thermal cue includes one or more points on the thermoelectric display 100 being configured to pulse according to one or more frequencies and at one or more temperatures. In these embodiments, as a user gets closer to their destination, the temperature of the one or more points gets hotter, and as the user gets further away from their destination, the temperature of the one or more points gets colder. In some embodiments, the thermal cue includes an indication of direction, as will be described herein below with reference to FIG. 6.

From operation 506, the method 500 proceeds to operation 508, wherein the mobile device triggers the thermal cue by instructing the thermoelectric display 100 to produce the thermal cue by heating and/or cooling one or more of the thermoelectric devices 102 in accordance with the thermal cue calculated at operation 506. From operation 508, the method 500 proceeds to operation 510. The method 500 ends at operation 510.

Figure 6:
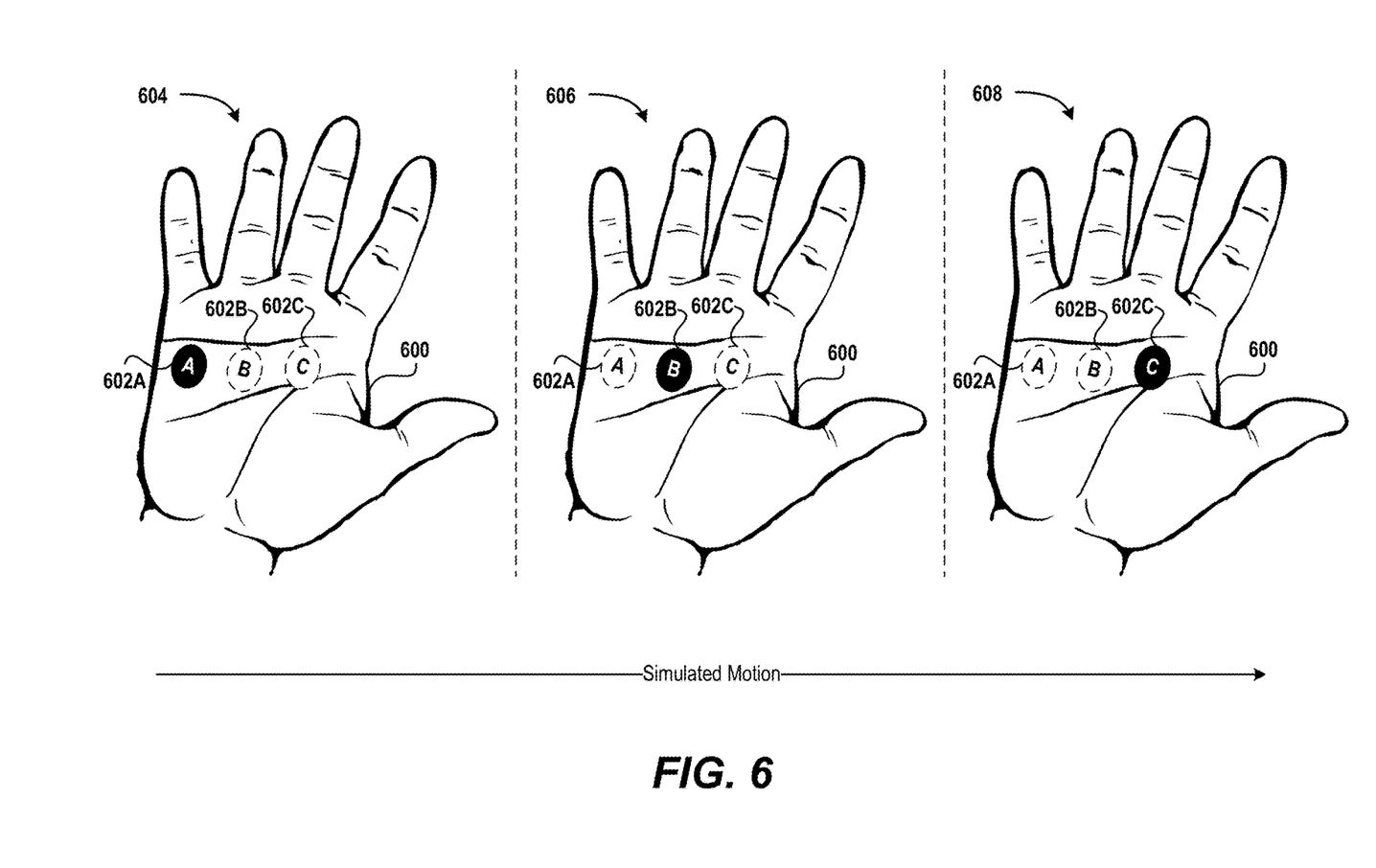
FIG. 6 is a diagram illustrating a user's hand undergoing a simulated rightward motion via thermal feedback provided by a thermoelectric display, according to an illustrative embodiment.

Turning now to FIG. 6, a user's hand 600 is illustrated with heat or cold being sensed by the user from a first thermal point 602A, to a second thermal point 602B, and then to a third thermal point 602C, thereby simulating a rightward motion via thermal feedback as an illustrative embodiment of a thermal cue. In particular, in a first state 604, the user's hand 600 senses a temperature change at the thermal point 602A, then, in a second state 606, the user's hand 600 senses a temperature change at the thermal point 602B, and then, in a third state 608, the user's hand 600 senses a temperature change at the thermal point 602C. The resulting sensation is used to simulate a rightward motion to the user thereby instructing the user to perform a right-hand turn. The illustrated embodiment is but one use of thermal feedback to indicate a direction to a user, such as in context of providing navigation instructions to the user. Other uses of thermal feedback in this and other contexts are contemplated.

Figure 7:
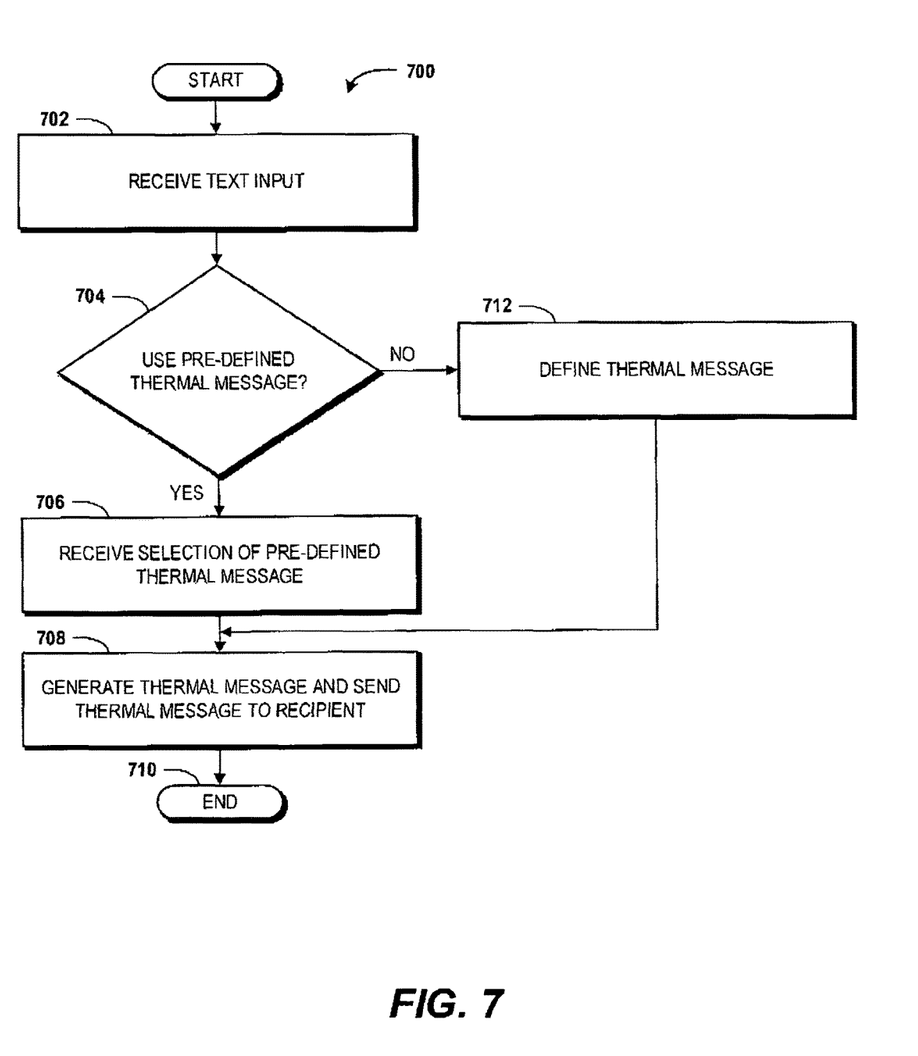
FIG. 7 is a flow diagram illustrating aspects of a method for generating and sending a thermal message, according to an illustrative embodiment.

Turning now to FIG. 7, a flow diagram illustrating a method 700 for generating and sending a thermal message to another device will be described, according to an illustrative embodiment. The method 700 is described in context of the thermoelectric display 100 being operatively coupled to another device. For ease of explanation and not limitation, the method 700 will be described in context of the thermoelectric display 100 being operatively coupled to a mobile device such as, but not limited to, a smartphone or other cellular telephone, a tablet, or other mobile computing device.

A thermal message, in some embodiments, is used in lieu of a text message to convey a message of a similar fashion. In some embodiments, a thermal message is sent in addition to a text message and upon receipt at the destination device, the thermal message and/or the text message is presented to the recipient based upon a setting on the destination device. In some embodiments, a thermal message is a pre-defined message. A pre-defined message may be defined by a user, a manufacturer of the mobile device, a wireless carrier providing wireless telecommunications service to the user, and/or a third party, such as an application provider. In some embodiments, a thermal message is defined by the user on the mobile device on-the-fly. Thermal messages defined in this manner may be saved for future use as a pre-defined message.

The method 700 begins at operation 702, wherein the mobile device receives text input. Text input may be received via a software keyboard, input to which is provided via a touchscreen and/or the thermoelectric display 100. Other inputs such as via a hardware keyboard, gesture inputs, voice inputs, and the like are contemplated.

From operation 702, the method 700 proceeds to operation 704, wherein it is determined if a pre-defined thermal message is to be used. If the mobile device determines, at operation 704, that a pre-defined thermal message is to be used, the method 700 proceeds to operation 706, wherein the mobile device receives a selection of a pre-defined thermal message. The selection may be performed by a user or automatically by the mobile device.

In some embodiments, the determination at operation 704 is based upon a user input indicating a user's desire to use a pre-defined thermal message. If the user desires to use a pre-defined thermal message, the user then selects a pre-defined thermal message at operation 706. In some embodiments, the text input received at operation 702 is compared to unique text that is associated with each of the available pre-defined thermal messages. In these embodiments, if a match exists between the text input and the unique text of one of the pre-defined thermal messages, it is determined, at operation 704, to use the matching pre-defined thermal message. In some embodiments, the text input need only match the unique text in context. For example, if the text input is determined to convey happiness, such as by the inclusion of well wishes, happy birthday, or the like, a pre-defined thermal message that is generic to these sentiments may be used.

From operation 706, the method 700 then proceeds to operation 708, wherein the mobile device generates a thermal message and sends the thermal message to a recipient. In some embodiments, the thermal message includes instructions indicating how one or more thermoelectric devices of a thermoelectric display associated with the destination device are to be manipulated to convey the thermal message to the recipient. Such instructions may include, but are not limited to, target temperature(s), target thermoelectric device(s), temperature variation(s), and/or one or more frequencies at which to generate heat or cold at one or more of the thermoelectric devices.

From operation 708, the method 700 proceeds to operation 710. The method 700 ends at operation 710.

If the mobile device determines, at operation 704, that a pre-defined thermal message is not to be used, the method 700 proceeds to operation 712, wherein the mobile device prompts the user to define a thermal message and receives input from the user to define a thermal message. In some embodiments, a thermal message is defined via a touch user interface through which a user selects all or a portion of a representative thermoelectric display. In these embodiments, the selections are translated into instructions to be provided in a thermal message to a destination device. Other inputs via keyboard, mouse, voice, gesture, and the like are contemplated.

From operation 712, the method 700 then proceeds to operation 708, wherein the mobile device generates a thermal message and sends the thermal message to a recipient. From operation 708, the method 700 proceeds to operation 710. The method 700 ends at operation 710.

Figure 8:
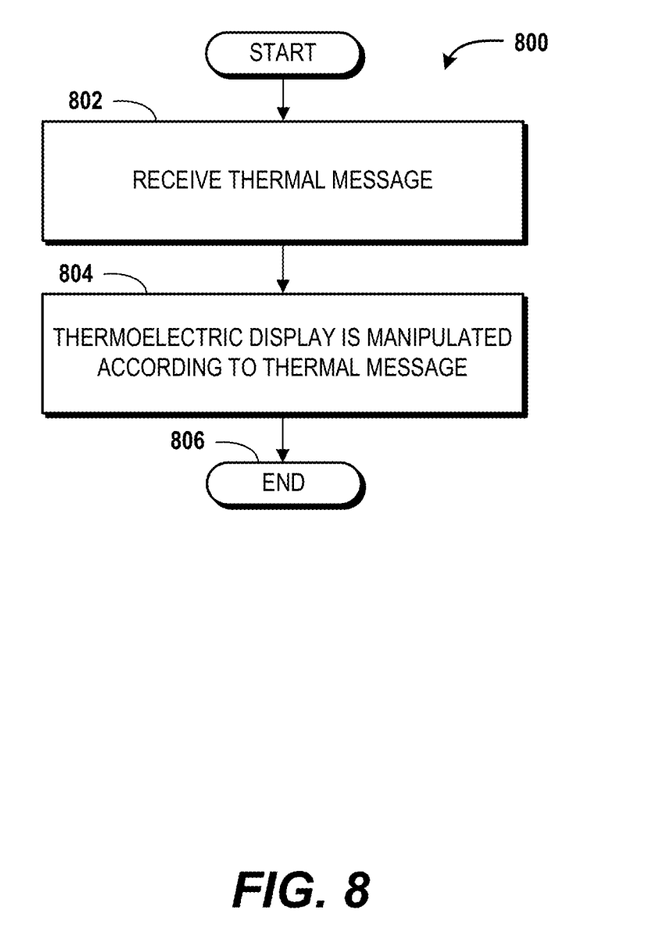
FIG. 8 is a flow diagram illustrating aspects of a method for receiving a thermal message and presenting the thermal message to a user via a thermoelectric display, according to an illustrative embodiment.

Turning now to FIG. 8, a flow diagram illustrating a method 800 for receiving a thermal message will be described, according to an illustrative embodiment. The method 800 is described in context of the thermoelectric display 100 being operatively coupled to another device. For ease of explanation and not limitation, the method 800 will be described in context of the thermoelectric display 100 being operatively coupled to a mobile device such as, but not limited to, a smartphone or other cellular telephone, a tablet, or other mobile computing device.

The method 800 begins at operation 802, wherein the mobile device receives a thermal message. From operation 802, the method 800 proceeds to operation 804, wherein the thermoelectric display 100 is manipulated according to instructions included in the thermal message. The method 800 then proceeds to operation 806. The method 800 ends at operation 806.

Figure 9:
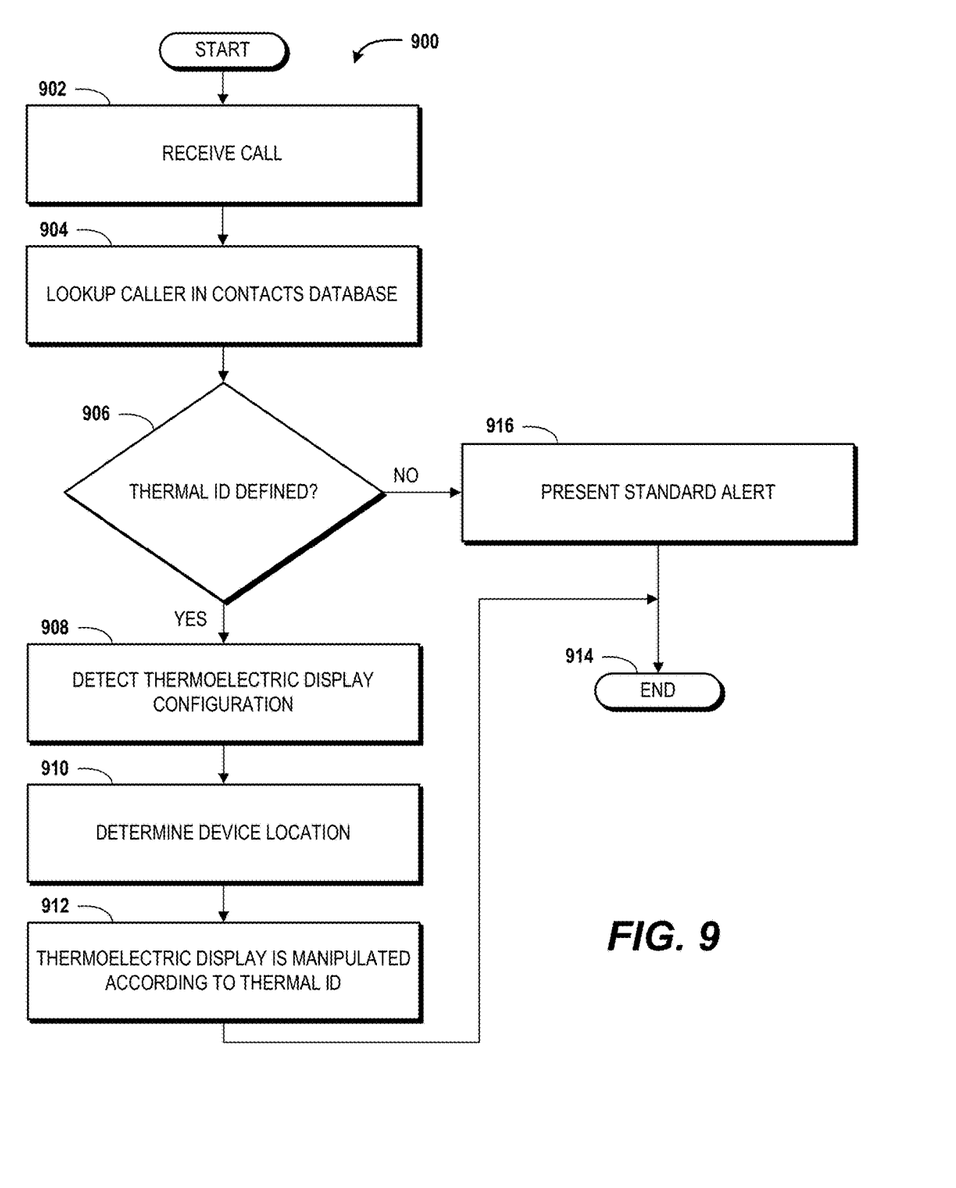
FIG. 9 is a flow diagram illustrating aspects of a method for receiving an incoming call and providing a thermal identification for the call, according to an illustrative embodiment.

Turning now to FIG. 9, a flow diagram illustrating a method 900 for receiving an incoming call will be described, according to an illustrative embodiment. The method 900 is described in context of the thermoelectric display 100 being operatively coupled to another device. For ease of explanation and not limitation, the method 900 will be described in context of the thermoelectric display 100 being operatively coupled to a mobile device such as, but not limited to, a smartphone or other cellular telephone, a tablet, or other mobile computing device.

The method 900 begins and proceeds to operation 902, wherein the mobile device receives an incoming call. From operation 902, the method 900 proceeds to operation 904, wherein the mobile device performs a lookup of the caller associated with the incoming call in a contacts database. In some embodiments, the contacts database is stored locally on the mobile device. In some embodiments, the contacts database is stored remotely on a network server. In some embodiments, contacts stored locally and remotely are synchronized.

From operation 904, the method 900 proceeds to operation 906, wherein the mobile device determines if a thermal identification is defined for the caller based upon the caller information available in the contacts database. In some embodiments, the thermal identification is a thermal image uniquely associated with a caller. In some embodiments, the thermal identification is a simulated motion, such as described above with respect to FIG. 6, uniquely associated with the caller. In some embodiments, the thermal identification is provided in addition to traditional caller identification. In some embodiments, the thermal identification is provided in lieu of traditional caller identification.

If the mobile device determines, at operation 906, that a thermal identification is defined for the caller, the method 900 proceeds from operation 906 to operation 908, wherein the mobile device detects a configuration of the thermoelectric display 100. The configuration of the thermoelectric display 100 includes the location of one or more of the plurality of thermoelectric devices 102. In some embodiments, the configuration is reconfigurable such that one or more of the thermoelectric devices 102 are deactivated. In some embodiments, the configuration of the thermoelectric display 100 is reconfigurable via software stored within a computer-readable memory of the mobile device and executed by a processor of the mobile device. In some embodiments, the configuration of the thermoelectric display 100 is static or non-configurable. In some embodiments, operation 908 is configured to be performed once such as during a setup process during which a thermal identification is defined for one or more contacts. This may be the case for embodiments in which the thermoelectric display 100 is non-configurable. Alternatively, in some embodiments, operation 908 is performed each time the method 900 is executed.

From operation 908, the method 900 proceeds to operation 910, wherein the mobile device detects its location. In some embodiments, the mobile device determines its location in accordance with the method 400 described herein above with reference to FIG. 4. From operation 910, the method 900 proceeds to operation 912, wherein the thermoelectric display is manipulated according to the thermal identification to provide thermal feedback to the user to identify the caller. The method 900 then proceeds to operation 914. The method 900 ends at operation 914.

If the mobile device determines, at operation 906, that a thermal identification is not defined for the caller, the method 900 proceeds from operation 906 to operation 916. At operation 916, the mobile device presents a standard caller alert, such as a ringtone and/or vibration. The method 900 then proceeds to operation 914, wherein the method 900 ends.

Figure 10:
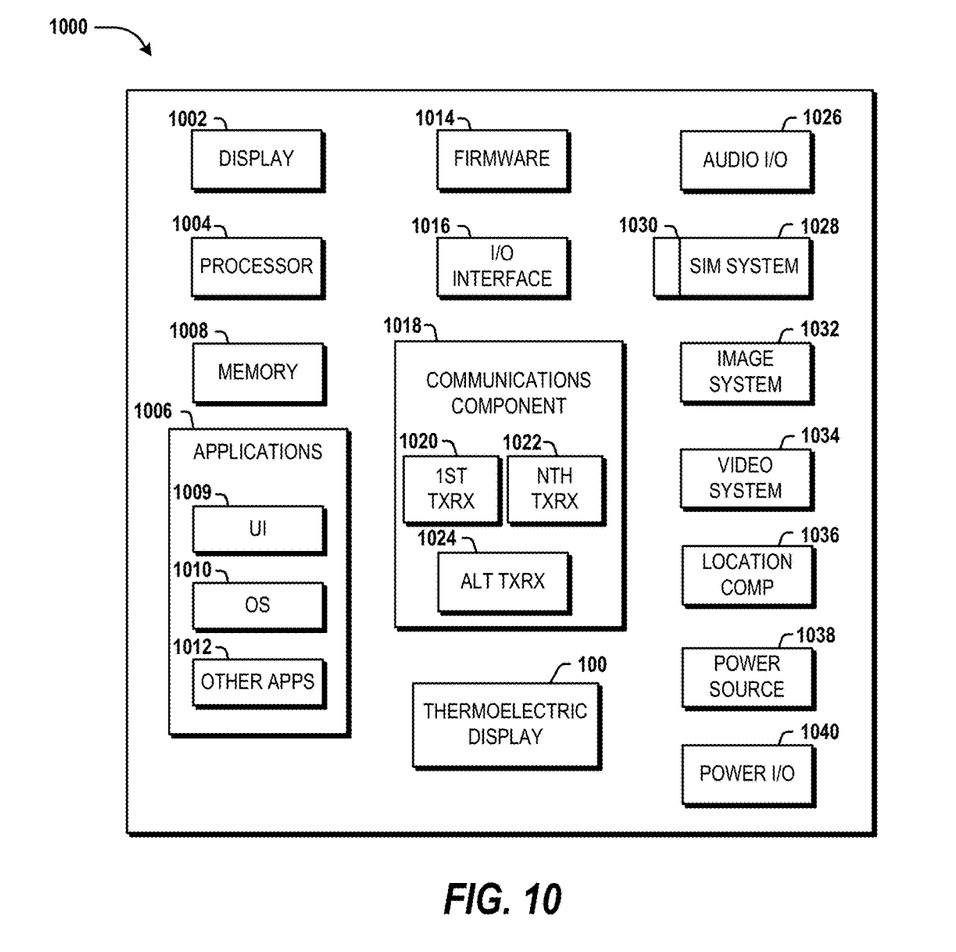
FIG. 10 is a mobile device architecture diagram illustrating an illustrative mobile device hardware and software architecture for a mobile device capable of implementing aspects of the embodiments disclosed herein.

Turning now to FIG. 10, an illustrative mobile device 1000 and components thereof will be described. Although connections are not shown between the components illustrated in FIG. 10, the components can interact with each other to carry out device functions. In some embodiments, for example, the components are arranged so as to communicate via one or more busses (not shown). It should be understood that FIG. 10 and the following description are intended to provide a general understanding of a suitable environment in which various aspects of embodiments can be implemented. The mobile device described herein above may be configured like the mobile device 1000. It should be understood that the mobile device may include additional functionality or include less functionality than now described.

As illustrated in FIG. 10, the mobile device 1000 includes a display 1002 for visually displaying data including, but not limited to, graphical user interface ("GUI") elements, text, images, video, virtual keypads and/or keyboards, messaging data, notification messages, metadata, internet content, device status, time, date, calendar data, device preferences, map and location data, and the like. The mobile device 1000 also includes a processor 1004 for processing data and/or executing computer-executable instructions of one or more applications 1006 stored in a memory 1008. In some embodiments, the applications 1006 include a UI application 1009. The UI application 1009 interfaces with an operating system ("OS") application 1010 to facilitate user interaction with device functionality and data. In some embodiments, the OS application 1010 is one of SYMBIAN OS from SYMBIAN LIMITED, WINDOWS MOBILE OS from MICROSOFT CORPORATION, WINDOWS PHONE OS from MICROSOFT CORPORATION, PALM WEBOS from HEWLETT PACKARD CORPORATION, BLACKBERRY OS from RESEARCH IN MOTION LIMITED, IOS from APPLE INC., and ANDROID OS from GOOGLE INC. These operating systems are merely illustrative of the operating systems that may be used in accordance with the embodiments disclosed herein.

The UI application 1009 aids a user in activating service over-the-air, if applicable, defining thermal messages, defining thermal identifications, entering message content, viewing received messages, answering/initiating calls, entering/deleting data, entering and setting user IDs and passwords for device access, configuring settings, manipulating contacts database content and/or settings, multimode interaction, interacting with other applications 1012, and otherwise facilitating user interaction with the OS application 1010 and the other applications 1012.

In some embodiments, the other applications 1012 include thermal applications configured to perform the various embodiments described herein for using the thermoelectric display 100 as an output device and for using the thermoelectric display 100 as an input device. In some embodiments, the other applications 1012 include, for example, presence applications, visual voicemail applications, messaging applications, text-to-speech and speech-to-text applications, add-ons, plug-ins, email applications, music applications, video applications, camera applications, location-based service applications, navigation applications, power conservation applications, game applications, productivity applications, entertainment applications, enterprise applications, combinations thereof, and the like. The applications 1006 or portions thereof are stored in the memory 1008 and/or in a firmware 1014, and are executed by the processor 1004. The firmware 1014 may also store code for execution during device power up and power down operations. In some embodiments, the OS 1010 or a portion thereof, such as a kernel, is stored in the firmware 1014.

The mobile device 1000 also includes an input/output ("I/O") interface 1016 for the input/output of data such as location information, presence status information, user IDs, passwords, application initiation (start-up) requests, and other input/output of data associated with the embodiments disclosed herein. In some embodiments, the I/O interface 1016 is a hardwire connection such as a universal serial bus ("USB"), mini-USB, micro-USB, audio jack, PS2, IEEE 1394, serial, parallel, Ethernet (RJ45) port, RJ11 port, proprietary port, combinations thereof, or the like. In some embodiments, the mobile device 1000 is configured to synchronize with another device (e.g., a computer) to transfer content stored to/from the mobile device 1000. In some embodiments, the mobile device 1000 is configured to receive updates to one or more of the applications 1006 via the I/O interface 1016. In some embodiments, the I/O interface 1016 accepts I/O devices such as keyboards, keypads, mice, interface tethers, printers, plotters, external storage, touch/multi-touch screens, touch pads, trackballs, joysticks, microphones, remote control devices, displays, projectors, medical equipment (e.g., stethoscopes, heart monitors, and other health metric monitors), modems, routers, external power sources, docking stations, combinations thereof, and the like. It should be appreciated that the I/O interface 1016 may be used for communications between the mobile device 1000 and a network device or local device instead of, or in addition to, a communications component 1018.

The communications component 1018 interfaces with the processor 1004 to facilitate wireless communications with one or more networks. In some embodiments, the one or more networks include networks that utilize a cellular wireless technology. In some embodiments, one or more networks include networks that utilize non-cellular wireless technologies such as WI-FI or WIMAX. In some embodiments, the communications component 1018 includes a multimode communications subsystem for facilitating communications via a cellular network and one or more WI-FI, WIMAX or other non-cellular wireless network.

The communications component 1018, in some embodiments, includes one or more transceivers each configured to communicate over the same or a different wireless technology standard. For example, the transceivers of the communications component 1018 may be configured to communicate using Global System for Mobile communications ("GSM"), Code Division Multiple Access ("CMDA") One ("CDMAONE"), CDMA2000, Long Term Evolution ("LTE"), and various other 2G, 2.5G, 3G, 4G, and greater generation technology standards. Moreover, the communications component 1018 may facilitate communications over various channel access methods (which may or may not be used by the aforementioned standards) including, but not limited to, Time Division Multiple Access ("TDMA"), Frequency Division Multiple Access ("FDMA), Wideband CDMA ("W-CDMA"), Orthogonal Frequency Division Multiplexing ("OFDM"), Space-Division Multiple Access ("SDMA"), and the like. In addition, the communications component 1018 may facilitate data communications using General Packet Radio Service ("GPRS"), Enhanced Data Rates for GSM Evolution ("EDGE"), the High Speed Packet Access ("HSPA") protocol family including High Speed Downlink Packet Access ("HSDPA"), Enhanced Uplink ("EUL") or otherwise termed High Speed Uplink Packet Access ("HSUPA"), HSPA+, and various other current and future wireless data access standards.

In the illustrated embodiment, the communications component 1018 includes a first cellular transceiver 1020 that operates in one mode (e.g., GSM), and an $N^{th}$ cellular transceiver 1022 operates in a different mode (e.g., UMTS). While only two cellular transceivers 1020, 1022 are illustrated, it should be appreciated that more than two transceivers can be included in the communications component 1018.

The illustrated communications component 1018 also includes an alternative communications transceiver 1024 for use by other communications technologies including WI-FI, WIMAX, BLUETOOTH, infrared, infrared data association ("IRDA"), near field communications ("NFC"), other RF, combinations thereof, and the like. In some embodiments, the communications component 1018 also facilitates reception from terrestrial radio networks, digital satellite radio networks, internet-based radio service networks, combinations thereof, and the like.

The communications component 1018 processes data from a network such as an internet, the Internet, an intranet, a home broadband network, a WI-FI hotspot, and the like, via an internet service provider ("ISP"), digital subscriber line ("DSL") provider, or broadband provider.

Audio capabilities for the mobile device 1000 may be provided by an audio I/O component 1026 that includes a speaker for the output of audio signals and a microphone to collect audio signals.

The illustrated mobile device 1000 also includes a universal subscriber identity module ("USIM") system 1028 that includes a SIM slot interface 1030 for accommodating a USIM card. In some embodiments, the USIM system 1028 is configured to accept insertion of other SIM cards for access to other network types such as GSM. In other embodiments, the USIM system 1028 is configured to accept multiple SIM cards. In still other embodiments, the USIM system 1028 is configured to accept a universal integrated circuit card ("UICC") with one or more SIM applications stored thereupon.

The mobile device 1000 may also include an image capture and processing system 1032 ("image system"). Photos may be obtained via an associated image capture subsystem of the image system 1032, for example, a camera. The mobile device 1000 may also include a video system 1034 for capturing, processing, recording, and/or modifying video content. Photos and videos obtained using the image system 1032 and the video system 1034, respectively, may be added as message content to a multimedia message service ("MMS") message and sent to another mobile device.

The illustrated mobile device 1000 also includes a location component 1036 for sending and/or receiving signals such as global positioning system ("GPS") data, assisted-GPS data, WI-FI/WIMAX and/or cellular network triangulation data, combinations thereof, and the like, for determining a location of the mobile device 1000. The location component 1036 may communicate with the communications component 1018 to retrieve triangulation data for determining a location of the mobile device 1000. In some embodiments, the location component 1036 interfaces with cellular network nodes, telephone lines, satellites, location transmitters and/or beacons, wireless network transmitters and receivers, combinations thereof, and the like. In some embodiments, the location component 1036 includes one or more sensors such as a compass, an accelerometer, and/or a gyroscope to determine the orientation of the mobile device 1000. Using the location component 1036, the mobile device 1000 can generate and/or receive data to identify its location, or transmit data used by other devices to determine the location of the mobile device 1000. The location component 1036 may include multiple components for determining the location and/or orientation of the mobile device 1000.

The illustrated mobile device 1000 also includes a power source 1038, such as one or more batteries and/or other power subsystem (AC or DC). The power source 1038 may interface with an external power system or charging equipment via a power I/O component 1040.

The illustrated mobile device 1000 also includes the thermoelectric display 100. In some embodiments, the thermoelectric display 100 is built-in to the mobile device 1000.

In other embodiments, the thermoelectric display 100 is provided as an add-on to the mobile device 1000.

As used herein, communication media includes computer readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared, and other wireless media. Combinations of the any of the above should also be included within the scope of computer-readable media.

By way of example, and not limitation, computer storage media may include volatile and non-volatile, removable and non-removable media implemented in any method or technology for storage of information such as computer-readable instructions, data structures, program modules, or other data. For example, computer media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the mobile device 1000 or other devices or computers described herein. For purposes of the claims, the phrase "computer storage medium" and variations thereof, does not include waves, signals, and/or other transitory and/or intangible communication media, per se.

Encoding the software modules presented herein also may transform the physical structure of the computer-readable media presented herein. The specific transformation of physical structure may depend on various factors, in different implementations of this description. Examples of such factors may include, but are not limited to, the technology used to implement the computer-readable media, whether the computer-readable media is characterized as primary or secondary storage, and the like. For example, if the computer-readable media is implemented as semiconductor-based memory, the software disclosed herein may be encoded on the computer-readable media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the mobile device 1000 in order to store and execute the software components presented herein. It is also contemplated that the mobile device 1000 may not include all of the components shown in FIG. 10, may include other components that are not explicitly shown in FIG. 10, or may utilize an architecture completely different than that shown in FIG. 10.

Based on the foregoing, it should be appreciated that technologies for providing device feedback and input via heating and cooling have been disclosed herein. Although the subject matter presented herein has been described in language specific to computer structural features, methodological and transformative acts, specific computing machinery, and computer readable media, it is to be understood that the invention defined in the appended claims is not necessarily limited to the specific features, acts, or media described herein. Rather, the specific features, acts and mediums are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

We claim:

1. A mobile device comprising:
   a display comprising a plurality of layers, wherein the plurality of layers comprises a first layer comprising a touchscreen and a second layer comprising a thermoelectric display, wherein the thermoelectric display comprises an array of thermoelectric devices;
   a processor; and
   memory comprising instructions that, when executed by the processor, cause the processor to perform operations comprising
      prompting, via a user interface presented on the display, a user to position the mobile device in a location,
      acquiring a temperature reading from the thermoelectric display while the mobile device is in the location,
      associating the temperature reading with the location in a temperature classifier,
      storing the temperature classifier in a database, wherein the database stores a plurality of temperature classifiers,
      detecting a temperature change in at least a portion of the array of thermoelectric devices of the thermoelectric display,
      in response to detecting the temperature change, acquiring a further temperature reading from the thermoelectric display,
      comparing the further temperature reading to the plurality of temperature classifiers stored in the database,
      determining, based upon comparing the further temperature reading to the plurality of temperature classifiers stored in the database, that the temperature classifier corresponds to the further temperature reading,
      determining, based upon the temperature classifier corresponding to the further temperature reading, that the mobile device is in the location, and
      outputting the location to an application that is executable by the processor to perform a function based upon the mobile device being in the location.

2. The mobile device of claim 1, wherein the location is on the user.

3. The mobile device of claim 1, wherein the location is on an article of clothing associated with the user.

4. The mobile device of claim 1, wherein the location is within an article of clothing associated with the user.

5. The mobile device of claim 1, wherein the location is on an accessory associated with the user.

6. The mobile device of claim 1, wherein the location is within an accessory associated with the user.

7. A computer-readable storage medium having computer-executable instructions stored thereon that, when executed by a processor of a mobile device, cause the processor to perform operations comprising:
prompting, via a user interface presented on a display of the mobile device, a user to position the mobile device in a location;
acquiring a temperature reading from a thermoelectric display while the mobile device is in the location;
associating the temperature reading with the location in a temperature classifier;
storing the temperature classifier in a database, wherein the database stores a plurality of temperature classifiers;
detecting a temperature change in at least a portion of an array of thermoelectric devices of the thermoelectric display;
in response to detecting the temperature change, acquiring a further temperature reading from the thermoelectric display;
comparing the further temperature reading to the plurality of temperature classifiers stored in the database;
determining, based upon comparing the further temperature reading to the plurality of temperature classifiers stored in the database, that the temperature classifier corresponds to the further temperature reading;
determining, based upon the temperature classifier corresponding to the further temperature reading, that the mobile device is in the location; and
outputting the location to an application that is executable by the processor to perform a function based upon the mobile device being in the location.

8. The computer-readable storage medium of claim 7, wherein the location is on the user.

9. The computer-readable storage medium of claim 7, wherein the location is on the article of clothing associated with the user.

10. The computer-readable storage medium of claim 7, wherein the location is within an article of clothing associated with the user.

11. The computer-readable storage medium of claim 7, wherein the location is on an accessory associated with the user.

12. The computer-readable storage medium of claim 7, wherein the location is within an accessory associated with the user.

13. A method comprising:
prompting, by a mobile device comprising a processor, via a user interface presented on a display of the mobile device, a user to position the mobile device in a location;
acquiring, by the mobile device, a temperature reading from a thermoelectric display of the mobile device while the mobile device is in the location;
associating, by the mobile device, the temperature reading with the location in a temperature classifier;
storing, by the mobile device, the temperature classifier in a database, wherein the database stores a plurality of temperature classifiers;
detecting, by the mobile device, a temperature change in at least a portion of an array of thermoelectric devices of the thermoelectric display;
in response to detecting the temperature change, acquiring, by the mobile device, a further temperature reading from the thermoelectric display;
comparing, by the mobile device, the further temperature reading to the plurality of temperature classifiers stored in the database;
determining, by the mobile device, based upon comparing the further temperature reading to the plurality of temperature classifiers stored in the database, that the temperature classifier corresponds to the further temperature reading;
determining, by the mobile device, based upon the temperature classifier corresponding to the further temperature reading, that the mobile device is in the location; and
outputting, by the mobile device, the location to an application that is executable by the processor to perform a function based upon the mobile device being in the location.

14. The method of claim 13, wherein the location is on the user.

15. The method of claim 13, wherein the location is on an article of clothing associated with the user.

16. The method of claim 13, wherein the location is within an article of clothing associated with the user.

17. The method of claim 13, wherein the location is on an accessory associated with the user.

18. The method of claim 13, wherein the location is within an accessory associated with the user.

* * * * *